(12) United States Patent
Yan et al.

(10) Patent No.: US 11,852,573 B2
(45) Date of Patent: Dec. 26, 2023

(54) DETECTION DEVICE FOR PROTEIN IN URINE

(71) Applicant: Taiwan RedEye Biomedical Inc., Hsinchu (TW)

(72) Inventors: Shuo-Ting Yan, Hsinchu (TW); Ya-Ling Chiang, Hsinchu (TW)

(73) Assignee: Taiwan RedEye Biomedical Inc., Hsinchu (TW)

( * ) Notice: Subject to any disclaimer, the term of this patent is extended or adjusted under 35 U.S.C. 154(b) by 210 days.

(21) Appl. No.: 17/508,392

(22) Filed: Oct. 22, 2021

(65) Prior Publication Data

US 2023/0126078 A1   Apr. 27, 2023

(51) Int. Cl.
| | |
|---|---|
| *G01N 13/02* | (2006.01) |
| *G01N 33/493* | (2006.01) |
| *G01N 1/14* | (2006.01) |
| *G06N 5/022* | (2023.01) |

(52) U.S. Cl.
CPC .............. *G01N 13/02* (2013.01); *G01N 1/14* (2013.01); *G01N 33/493* (2013.01); *G01N 2013/0241* (2013.01); *G06N 5/022* (2013.01)

(58) Field of Classification Search
CPC ........ G01N 13/02; G01N 1/14; G01N 33/493; G01N 2013/0241; G06N 5/022
USPC ...................................................... 73/61.41
See application file for complete search history.

(56) References Cited

U.S. PATENT DOCUMENTS

| | | | | |
|---|---|---|---|---|
| 2001/0031500 A1* | 10/2001 | Kawamura | ............ | G01N 21/51 436/55 |
| 2005/0101028 A1* | 5/2005 | Kawamura | ............. | B01F 25/21 436/164 |
| 2016/0016172 A1 | 1/2016 | Pollack et al. | | |
| 2017/0227435 A1* | 8/2017 | Siedel | ................... | G01N 13/02 |

FOREIGN PATENT DOCUMENTS

| | | | | | |
|---|---|---|---|---|---|
| CA | 3052985 A1 | * | 8/2018 | ........ | B01L 3/502707 |
| CN | 110108891 A | | 8/2019 | | |
| CN | 111684285 A | | 9/2020 | | |
| DE | 102004040336 A1 | * | 2/2006 | ............. | G01N 13/02 |
| JP | H02208300 A | * | 8/1990 | | |

* cited by examiner

*Primary Examiner* — Marrit Eyassu
(74) *Attorney, Agent, or Firm* — RABIN & BERDO, P.C.

(57) ABSTRACT

The present invention includes a needle connected to a urine container; a side of the needle is connected to the urine container, and the other side is a blunt end; a holder is mounted on a base, and the urine container is detachably mounted on the holder; a camera unit is mounted on the base, aiming at the blunt end; a light source is mounted on the base, emitting a detection beam; a processor unit is electrically connected to the camera unit; wherein when a sample urine in the urine container drips through the needle and forms a drop of urine, the detection beam passes through the drop of urine and travels into the camera unit; the processor unit receives an image of the drop of urine through the camera unit, and the processor unit instantly calculates a protein concentration of the drop of urine from the image.

13 Claims, 6 Drawing Sheets

DETECTION DEVICE FOR PROTEIN IN URINE

BACKGROUND OF THE INVENTION

1. Field of the Invention

The present invention relates to a detection device for protein in urine, more particularly a detection device for protein in urine that determines protein concentration in urine optically.

2. Description of the Related Art

Protein is an essential constituent of human blood. Normally when blood circulates around a human body, parts of protein will be first filtered in the kidneys, and then re-enter into the blood stream once more. However, when the kidneys are malfunctioning, the kidneys fail to filter proteins properly, and a part of protein in the blood stream will leak into a person's urine, thus a person will experience proteinuria and have large concentration of albumin in the urine. Albumin is a type of protein, and proteinuria refers to having large concentration of protein, such as albumin, present in a person's urine.

Currently, one of the most used urine protein detection methods is a dipstick urinalysis. The dipstick urinalysis uses a chemical called tetrabromophenol blue (TBPB) as a color-changing indicator for pH scale changes of a person's urine. The color can change ranging from yellowish-green to bluish-green color depending on the pH scale changes. However, the dipstick urinalysis takes about 30 to 60 seconds to complete. This underwhelming processing time is too long to satisfy a need for instantaneous results.

The resulting color indicator of the dipstick urinalysis must be first interpreted by human eyes in order to determine protein concentration of the urine. Depending on the interpretation, different people can see different results. This means the result may involve human bias. Further, the result of the dipstick urinalysis is presented in a concentration range instead of an absolute protein concentration value. This means the result lacks precise measurements. Furthermore, dipsticks used for the dipstick urinalysis method must be maintained to have same testing qualities free of storage degradations. However, well-maintained storage is hard, and as a result, the testing qualities of the dipsticks are often being questioned.

As mentioned, the current dipstick urinalysis method of testing the protein concentration of the urine can experience several problems. Those problems include long processing time, human bias in test results, lack of precise measurements, and requirement of well-maintained storage conditions.

SUMMARY OF THE INVENTION

The present invention provides a detection device for protein in urine. The detection device for protein in urine measures protein concentrations free of the aforementioned problems by using an optical analysis. The optical analysis is able to provide instantaneous results and precise measurements.

The detection device for protein in urine includes a urine container, a needle, a holder, a base, a camera unit, a light source, and a processor unit.

The urine container includes a urine containing area to contain a sample urine.

The needle is mounted at a bottom of the urine container, connects the urine containing area, and has a first side and a second side. The first side and the second side oppose each other; and the first side is connected to the urine containing area, while the second side has a blunt end.

The holder is mounted on the base. The urine container is detachably mounted on the holder, and the blunt end of the needle is mounted in suspension.

The camera unit is mounted on the base, and includes a lens. The lens of the camera unit is aimed at the blunt end.

The light source is mounted on the base, and emits a detection beam. The detection beam passes the blunt end and travels into the lens of the camera unit.

The processor unit electrically connects to the camera unit.

When the urine container contains the sample urine, the sample urine drips through a needle and forms a drop of urine.

After forming the drop of urine, the detection beam passes through the drop of urine and travels into the lens of the camera unit.

The processor unit receives an image of the drop of urine captured by the camera unit, and the processor unit calculates protein concentration of the drop of urine according to the image.

The present invention only requires a few seconds to obtain a measurement of the protein concentration, rather than a requirement of 30 to 60 seconds in the prior art. Compared to the dipstick urinalysis method, the present invention generates results must faster. The present invention also eliminates a storage requirement and an interpretation bias mentioned in the prior art. Furthermore, the processor unit of the present invention is able to determine the protein concentration of the drop of urine according to a linear relationship between averaged surface tension of the drop of urine and the protein concentration. As a result, the present invention is able to more precisely calculate the protein concentration than the dipstick urinalysis method in the prior art.

DETAILED DESCRIPTION OF THE INVENTION

Figure 1:
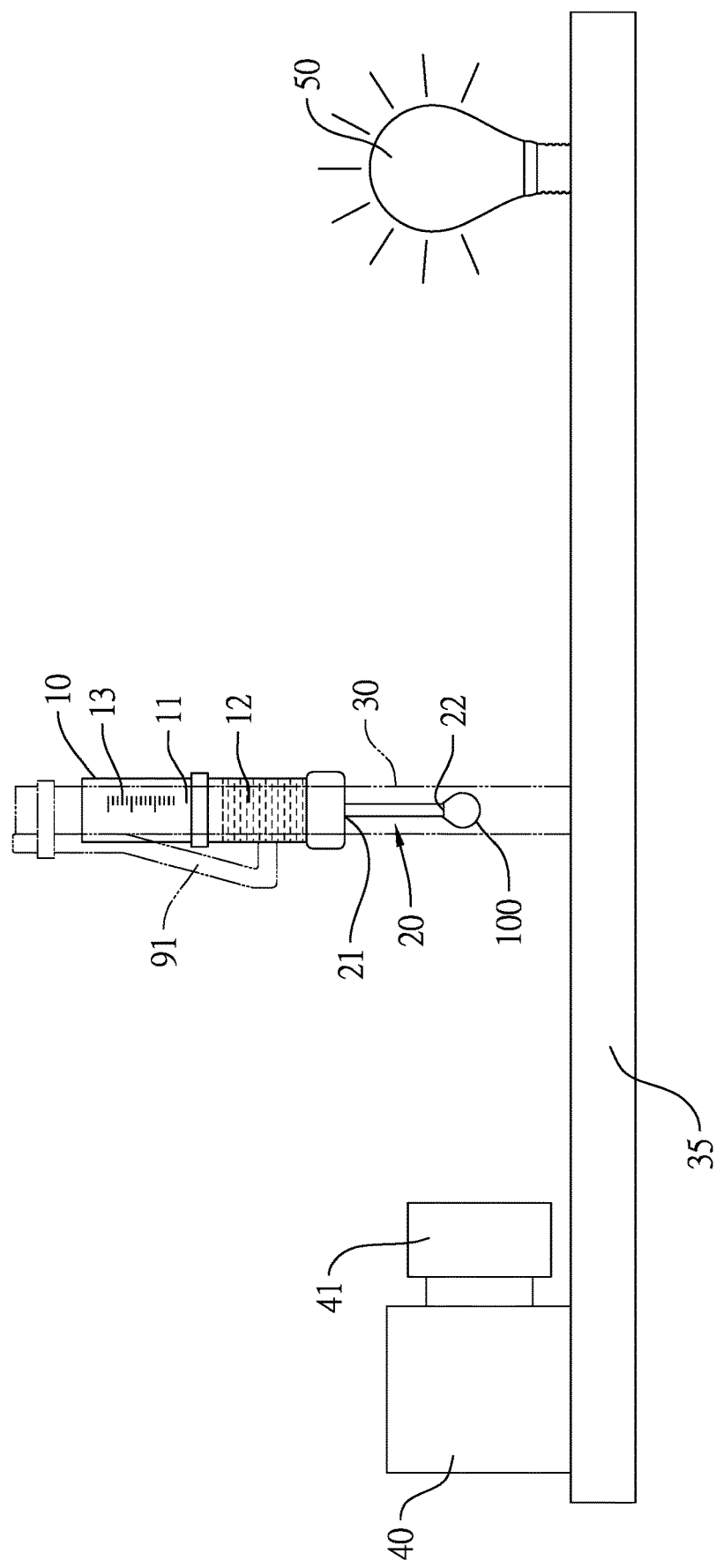
FIG. 1 is a perspective view of a detection device for protein in urine of the present invention.

With reference to FIG. 1, the present invention provides a detection device for protein in urine. The detection device for protein in urine includes a urine container 10, a needle 20, a holder 30, a base 35, a camera unit 40, a light source 50, and a processor unit 60.

The urine container 10 includes a urine containing area 11 to contain a sample urine 12. In an embodiment of the present invention, the urine container 10 is a transparent graduated container with graduations 13 thereon. Through the graduations 13, the sample urine 12 in the urine containing area 11 is able to show its volume.

The needle 20 is mounted at a bottom of the urine container 10. The needle 20 has a first side 21 and a second side, and the first side 21 and the second side are opposite to each other. The first side 21 of the needle 20 connects to the urine containing area 11, and the second side of the needle 20 has a blunt end 22. Further, the holder 30 is mounted on the base 35, and the urine container 10 is detachably mounted on the holder 30. This allows the blunt end 22 of the needle 20 to be mounted in suspension. When the urine container 10 contains the sample urine 12, the sample urine 12 drips through the needle 20 and forms a drop of urine 100.

In the present embodiment, when the sample urine 12 drips through the needle 20, the sample urine 12 forms the drop of urine 100 at the blunt end 22 of the needle 20.

The second side of the needle 20 has to have the blunt end 22, because the blunt end 22 is rotationally symmetric. The formation of the drop of urine 100 must be controlled with least variables possible to ensure a shape of the drop of urine 100 is uniform across each drip. In other words, each drip of the drop of urine 100 from the same sample urine 12 should in theory have the same shape. Since the blunt end 22 is rotationally symmetric, even if the blunt end 22 is slightly rotated, the shape of the drop of urine 100 will still be the same. To be more specific, when the drop of urine 100 is formed, if the drop of urine 100 is sliced horizontally parallel to the base 35, the present invention aims that the resulting cross-sections should all resemble circles due to rotational symmetry of the blunt end 22. If ends of other types are used for the needle 20, without rotational symmetry, the aforementioned cross-sections for the drop of urine 100 would resemble asymmetric ovals. The drop of urine 100 formed at the blunt end 22 should have the above mentioned rotational symmetry, as this is a basis of how the present invention measures protein concentration of the sample urine 12. Details of how the present invention measures the protein concentration will be discussed in later parts of the detailed description.

The camera unit 40 is mounted on the base 35, and the camera unit 40 includes a lens 41. The lens 41 of the camera unit 40 is aimed at the blunt end 22, or rather more particularly, the camera unit 40 is aimed at the drop of urine 100 formed at the blunt end 22 of the needle 20. The light source 50 is also mounted on the base 35, and the light source 50 emits a detection beam. The detection beam passes the blunt end 22 of the needle 20 into the lens 41 of the camera unit 40. In other words, when the drop of urine 100 is formed at the blunt end 22, the detection beam first passes through the drop of urine 100 and then travels further into the lens 41 of the camera unit 40.

The processor unit 60 is electrically connected to the camera unit 40, and the processor unit 60 obtains an image of the drop of urine 100 captured by the camera unit 40 through the camera unit 40. The processor unit 60 then calculates the protein concentration of the drop of urine 100 according to the image. More specifically, in the present embodiment, the processor unit 60 first calculates averaged surface tension of the drop of urine 100 according to the image, then the processor unit 60 further calculates the protein concentration of the drop of urine 100 according to the obtained averaged surface tension.

The processor unit 60 receives the image of the drop of urine 100 from the camera unit 40, in order to analyze the shape of the drop of urine 100. Through analyzing the shape of the drop of urine 100, the processor unit 60 is able to calculate the protein concentration of the drop of urine 100. Assuming the protein concentration is uniformly distributed inside the drop of urine 100, the drop of urine 100 would have the same protein concentration inside. Under this assumption, in order to maintain the same shape for each drip of the drop of urine 100, and in order to maintain a standard of measurement across the sample urine 12, the formation of the drop of urine 100 must have a fixed volume. In the current embodiment, a pressing unit 91 is used to control the fixed volume of the drop of urine 100. The pressing unit 91 is detachably mounted on the holder 30, and more particularly once the holder 30 fixes the pressing unit 91 in place, the pressing unit 91 is mounted on a side of the urine container 10. The pressing unit 91 is further electrically connected to the processor unit 60. The pressing unit 91 presses the side of the urine container 10, forming a first deformation on the urine container 10, and allowing the sample urine 12 to exit from the blunt end 22 of the needle 20 as the drop of urine 100 with a first volume. Since the first deformation on the urine container 10 is a fixed amount, the drop of urine 100 with the first volume exiting from the blunt end 22 of the needle 20 also has a fixed volume.

The processor unit 60 is further electrically connected to an input unit 80 and a display unit 70 respectively. The input unit 80 thus is electrically connected to the processor unit 60. When the input unit 80 starts, the input unit 80 sends a starting signal to the processor unit 60. When the processor unit 60 receives the starting signal, the processor unit 60 starts controlling the camera unit 40 to capture the image of the drop of urine 100. When the processor unit 60 receives the image, the processor unit 60 calculates the protein concentration of the drop of urine 100, and through the display unit 70, the processor unit 60 displays a measuring result of the protein concentration. In the current embodiment, the input unit 80 is a starting button. In another embodiment of the present invention, the input unit 80 is a touching unit, and the touching unit is a touch pad.

Furthermore, when the processor unit 60 receives the starting signal, the processor unit 60 starts the pressing unit 91 by controlling the pressing unit 91 to compress the side of the urine container 10. Since the pressing unit 91 is being controlled by the processor unit 60, a moving range of the pressing unit 91 is also controlled by the processor unit 60. This means an extend that the pressing unit 91 presses on the urine container 10 is also limited, in other words, the extend that the urine containing area 11 is squeezed and compressed due to deformations of the urine container 10 is also being controlled.

Figure 2:
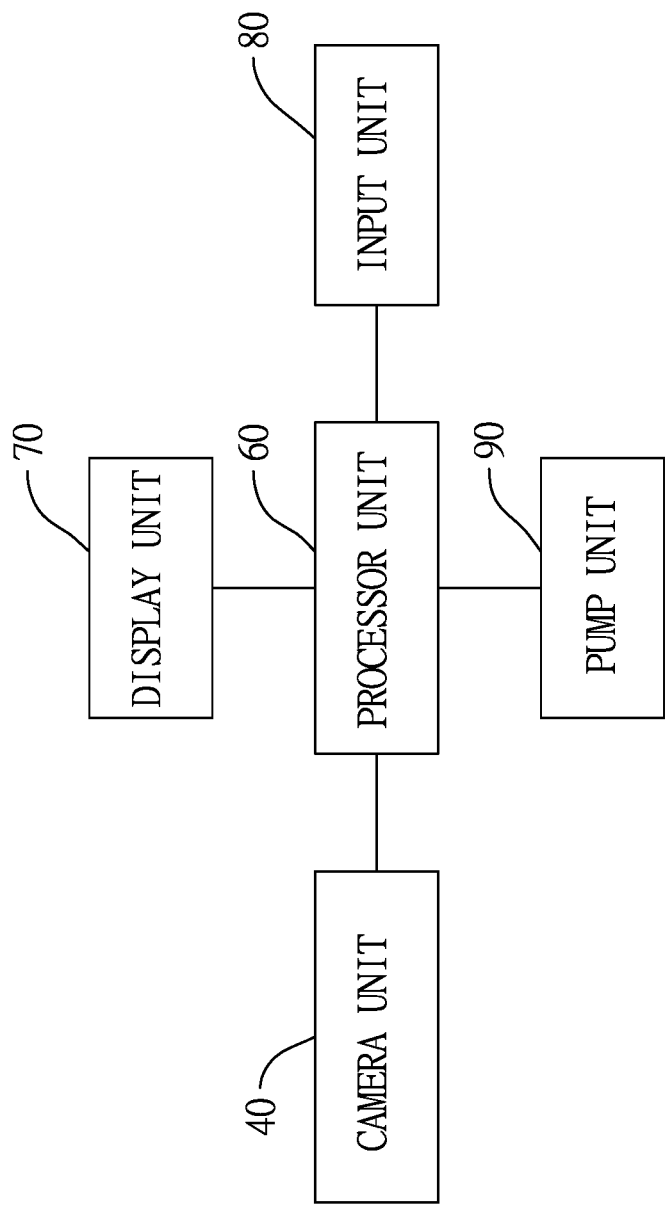
FIG. 2 is a block diagram of the detection device for protein in urine of the present invention.
Figure 3:
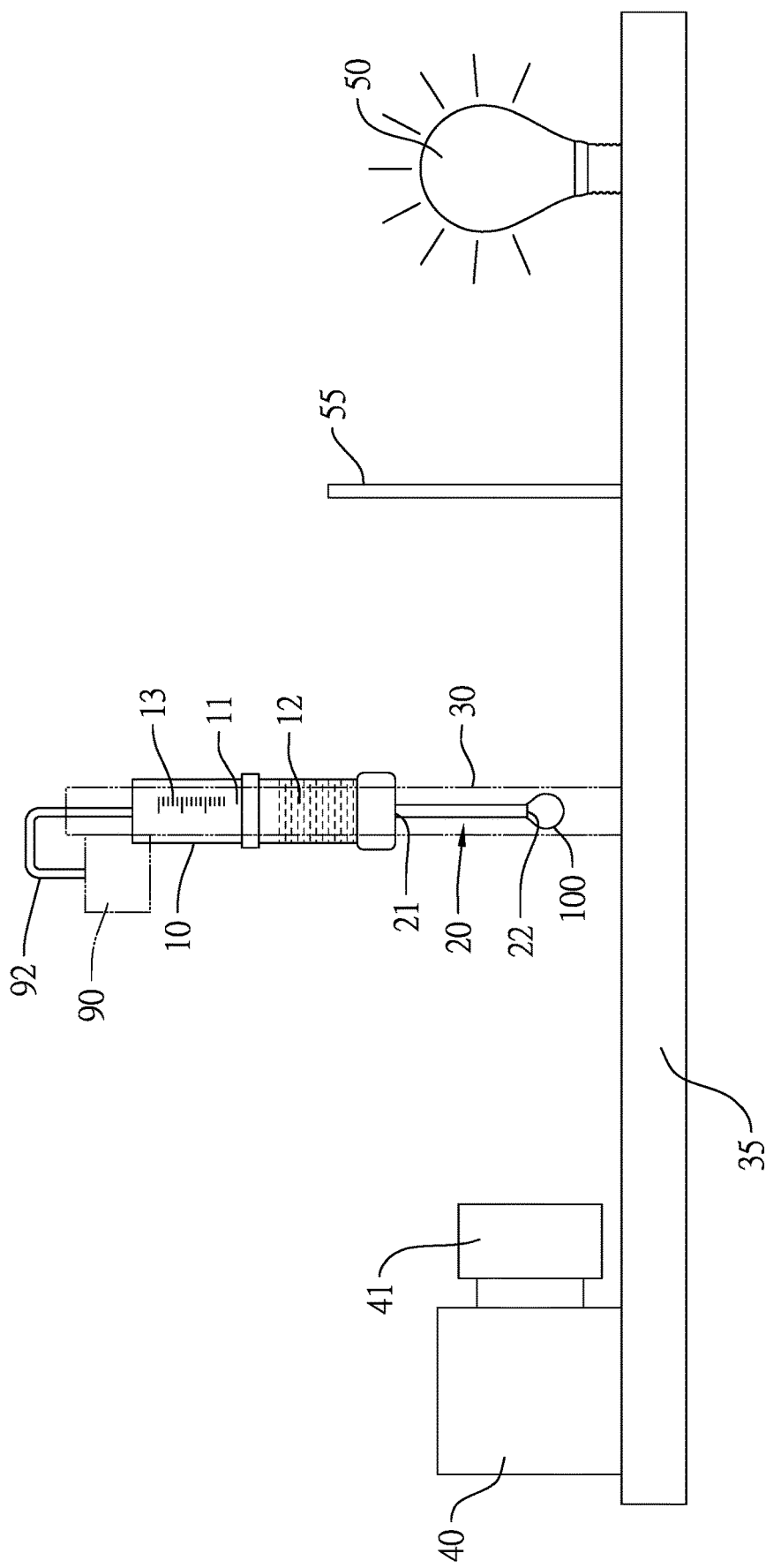
FIG. 3 is another perspective view of the detection device for protein in urine of the present invention.

With reference to FIGS. 2 and 3, in another embodiment, a pump unit 90 is used to control a fixed volume of the drop of urine 100. The pump unit 90 is detachably mounted on the holder 30, and the pump unit 90 is connected to a tube 92. The tube 92 connects the pump unit 90 to a top side of the urine container 10, allowing the pump unit 90 to transport and to output fluids through the tube 92 to the urine container 10. This way the pump unit 90 is able to squeeze out the drop of urine 100 by inputting fluids into the urine container 10 and raising an inner pressure of the urine container 10. The pump unit 90 is electrically connected to the processor unit 60. The processor unit 60 controls a pumping time and a pumping strength of the pump unit 90 outputting fluids. In another embodiment, the pump unit 90 can also output gas through the tube 92 into the urine container 10. The pump unit 90 may also be directly mounted on top of the urine container 10, to directly pressure the urine container 10 without the tube 92.

The pump unit 90 produces a first outputting speed, and the first outputting speed is being regulated by the processor unit 60. When the processor unit 60 receives the starting signal, the processor unit 60 starts the pump unit 90, allowing the pump unit 90 to work for a first working time before stopping. The processor unit 60 allows the pump unit 90 to output the drop of urine 100 of the sample urine 12 with the first volume from the urine container 10 to the blunt end 22 of the needle 20 with the first outputting speed.

Regarding both embodiments mentioned above, in reality units such as the pump unit 90 or the pressing unit 91 must consider pre-existing air in the needle 20 when squeezing the drop of urine 100 out of the urine container 10. In other words, when the urine container 10 is first mounted on the holder 30, the needle 20 is yet to contain the sample urine 12. Before the drop of urine 100 is squeezed out of the blunt end 22, the sample urine 12 would first need to fill the needle 20 up. The processor unit 60 first controls the unit responsible for squeezing out the drop of urine 100 to fill up the needle 20 with the sample urine 12, and only then the processor unit 60 starts ensuring the drop of urine 100 is formed out of the blunt end 22 with the first volume as described before. Since the needle 20 has a fixed amount of volume, the processor unit 60 is able to easily calculate a time needed for the sample urine 12 to fill up the needle 20 with the first outputting speed. The processor unit 60 first controls squeezing out the drop of urine 100 with a first preparation time for filling up the needle 20, and only then the processor unit 60 controls steadily outputting the drop of urine 100 with the first volume.

The detection device for protein in urine further includes a diffuser 55. The diffuser 55 is mounted between the light source 50 and the blunt end 22 of the needle 20. When the detection beam passes through the drop of urine 100 and travels into the lens 41 of the camera unit 40, here in detailed actuality, the detection beam first passes through the diffuser 55 before passing through the drop of urine 100 and traveling into the lens 41 of the camera unit 40. The diffuser 55 diffuses the detection beam so as to uniformly shine through the drop of urine 100. The detection beam emitted by the light source 50 is a white light. The light source 50 is a light bulb mounted on the base 35 that emits white light. An intensity of the white light is diffused and equally distributed across the diffuser 55, making the diffuser 55 resemble a screen of white light. The diffuser 55 evenly highlights the shape of the drop of urine 100, and projects the image into the camera unit 40, allowing the image to accurately show the shape of the drop of urine 100.

The urine container 10 and the needle 20 are both single-use equipment. Steps to utilize the present invention include the following:

placing different sets of the sample urine 12 into different urine containers;

wherein each of the urine containers is connected to a needle;

when measurements are needed, mounting a set of the urine container 10 with the needle 20 on the holder 30;

after measurements, removing the set of the urine container 10 with the needle 20 from the holder 30, and discarding the urine container 10 and the needle 20 into a specialized trash can for medical wastes.

When an equilibrium is reached between a surface tension and a gravitational force of the drop of urine 100 at the blunt end 22, the drop of urine 100 stops moving. Even though the camera unit 40 of the present invention is able to capture the drop of urine 100 in moving motions, the camera unit 40 still better captures the image when the drop of urine 100 stops moving, since this would allow better resolution for the image.

Figure 4:
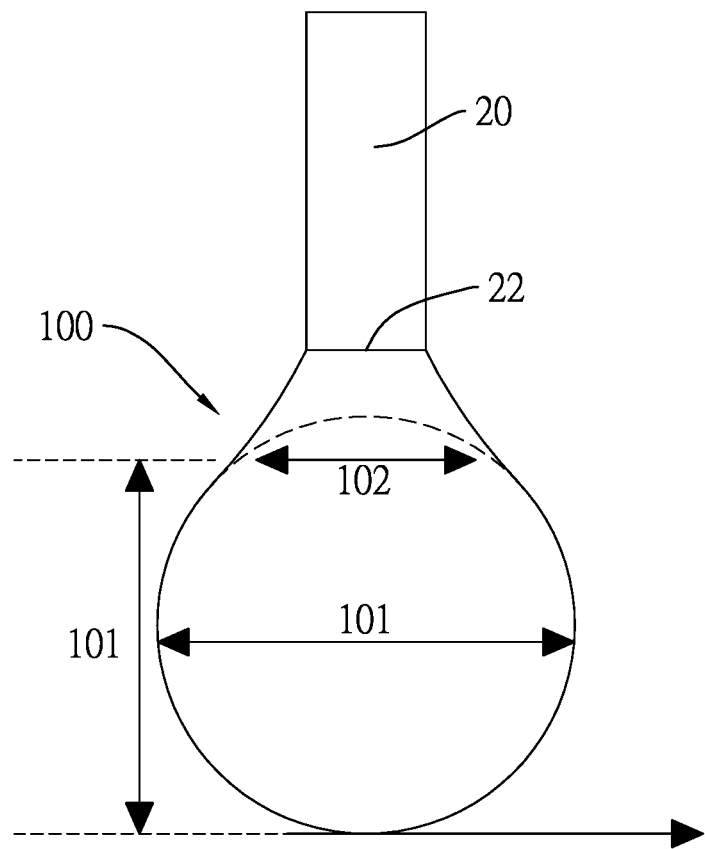
FIG. 4 is a perspective view of formation of a drop of urine at a blunt end of a needle of the detection device for protein in urine of the present invention.

With reference to FIG. 4, the drop of urine 100 of the image is shown in a perspective view. When the processor unit 60 receives the image of the drop of urine 100 through the camera unit 40, the processor unit 60 calculates a first drop diameter 101, a second drop diameter 102, and a correction coefficient. The first drop diameter 101 is the widest diameter of the drop of urine 100 in the image along a horizontal direction. The second drop diameter 102 is a diameter of a horizontal cross-section of the drop of urine 100 in the image. The horizontal cross-section is located vertically at the first drop diameter 101 length away from a most bottom point of the drop of urine 100 in the image. The correction coefficient is defined according to changes between the first drop diameter 101 and the second drop diameter 102.

The processor 60 of the present invention further calculates the averaged surface tension of the drop of urine 100 by using a pendant drop method based on the first drop diameter 101 and the second drop diameter 102. The pendant drop method is a method used to measure the averaged surface tension, and the pendant drop method has been developed since $19^{th}$ century. According to the pendant drop method, a shape of a suspended drop is factored by a volume, density, and surface/interface tension of a fluid being squeezed out. When applied to the present invention, the shape of the drop of urine 100 is determined by the volume, the density, and the surface tension of the sample urine 12 being squeezed out of the blunt end 22 of the needle 20. Since the density and the protein concentration of the drop of urine 100 are positively correlated, and since the volume of the drop of urine 100 is controlled, when the shape of the drop of urine 100 is being measured, the processor unit 60 is able to calculate the protein concentration. When the density of the drop of urine 100 is high, the protein concentration of the drop of urine 100 is also high. To be more specific, the density of the drop of urine 100 is determined relative to a background air density of where the pendant drop method is used. The present invention uses the following formula of the pendant drop method as a basis to calculate the averaged surface tension:

$$r = \Delta\rho * g * d_e^2 / H$$

wherein, r represents the averaged surface tension, $\Delta\rho$ represents a density difference between the density of the drop of urine 100 and the background air density, g represents a gravitational constant, $d_e$ represents the first drop diameter 101, and (1/H) represents the correction coefficient.

When the processor unit 60 calculates the averaged surface tension of the drop of urine 100 in the image, the processor unit 60 basically calculates the averaged surface tension according to the first drop diameter 101 defined from the image and the correction coefficient.

Figure 5:
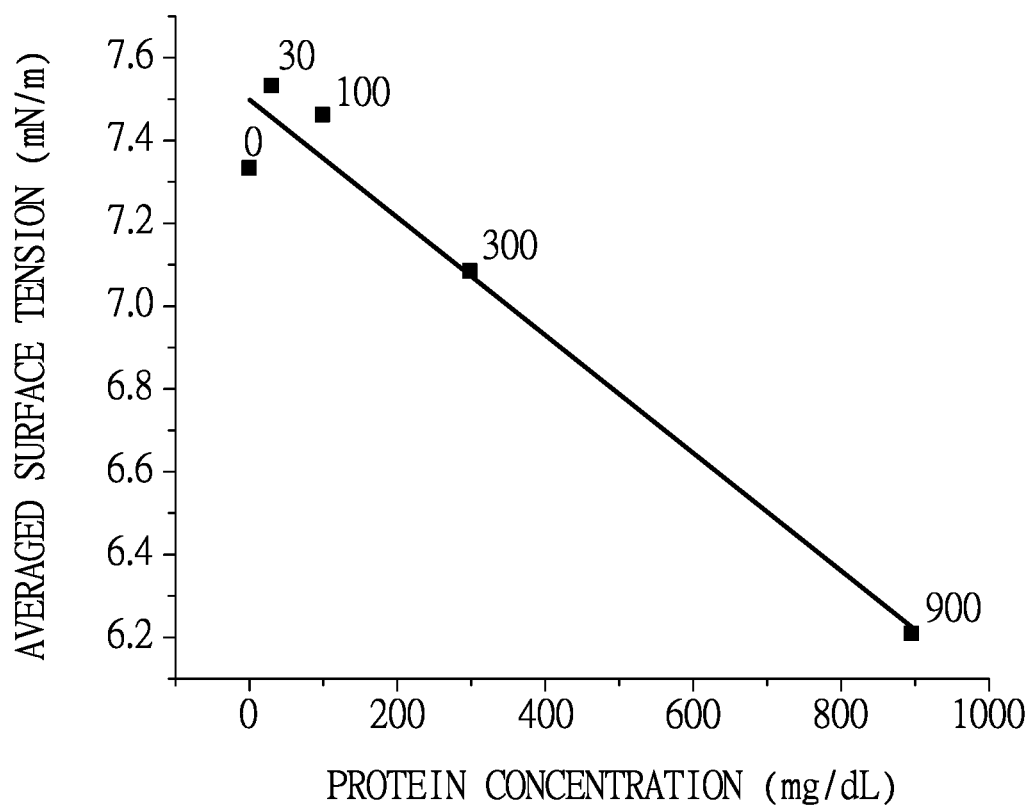
FIG. 5 is a conversion figure between averaged surface tension and protein concentration of the detection device for protein in urine of the present invention.

With reference to FIG. 5, the processor unit 60 stores a conversion table of averaged surface tension to urine protein concentration. The conversion table includes conversion data between the averaged surface tension and the protein concentration of urine. The conversion table is created through conducting experiments investigating relations of the averaged surface tension and the protein concentration of urine. When the processor unit 60 calculates the protein concentration of the drop of urine 100, which basically means according to the conversion table of averaged surface tension to urine protein concentration, the processor unit 60 converts the calculated surface tension of the drop of urine 100 in order to calculate the protein concentration of the drop of urine 100. With reference to FIG. 5, in the conversion table, the averaged surface tension and the protein concentration are linearly and inversely proportional to each other. The averaged surface tension is measured in units of milli-Newton per meter (mN/m), in other words, an averaged surface tension for each meter. The protein concentration is measured in units of milligram per deciliter (mg/dL).

For example, when the processor unit 60 determines the surface tension of the drop of urine 100 is 7.1 mN/m according to the image, the processor unit 60 can basically correlate the protein concentration of the drop of urine 100 to be 300 mg/dL according to the averaged surface tension to urine protein concentration conversion table. On the other hand, the processor unit 60 also can formulate a linear formula according to data collected according to the image, and further the processor unit 60 uses the linear formula to calculate the protein concentration for the drop of urine 100. For example, data collected according to the image is shown in Form 1:

Form 1.

| x (mg/dL) | y (mN/m) |
|---|---|
| 0 | 7.31 |
| 30 | 7.53 |
| 100 | 7.45 |
| 300 | 7.10 |
| 900 | 6.20 |

When the processor unit 60 determines the surface tension of the drop of urine 100 is 6.6 mN/m according to the image, according to Form 1, the linear formula can be:

$$y=-0.0014x+7.4933$$

wherein y represents the averaged surface tension inputted into the linear formula, and x represents the protein concentration of urine outputted from the linear formula. When the averaged surface tension inputted into the linear formula is 6.6 mN/m, then:

$$x=(y-7.4933)/(-0.0014)=(6.6-7.4933)/(-0.0014)\approx 638$$

wherein the processor unit 60 calculates the protein concentration of the drop of urine 100 is 638 mg/dL.

In the current embodiment, the processor unit 60 further displays the protein concentration result of 638 mg/dL through the display unit 70. The present invention calculates the protein concentration of urine in a matter of seconds, allowing the present invention to instantly and accurately calculate the protein concentration of the sample urine 12.

Figure 6:
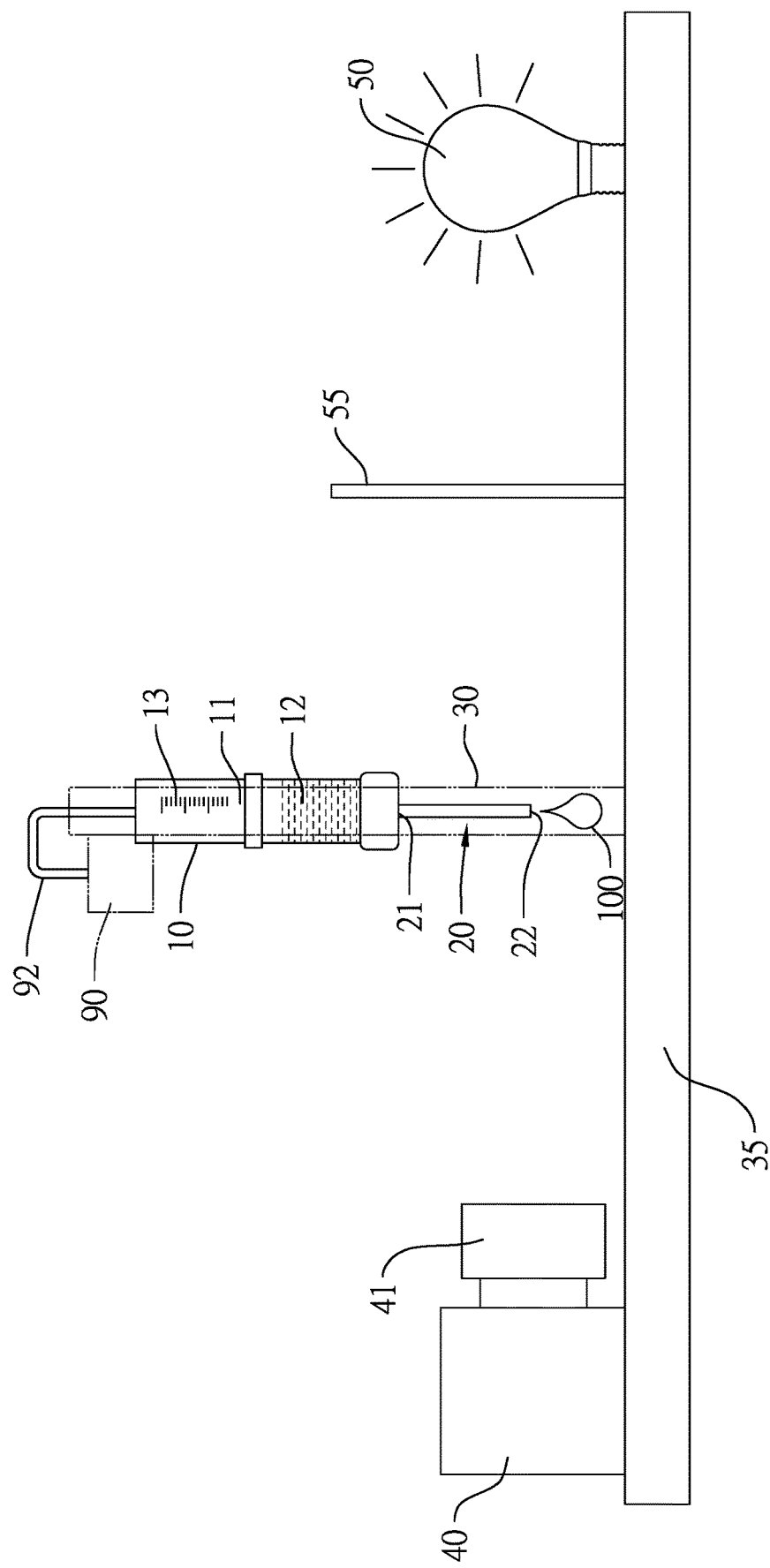
FIG. 6 is another perspective view of the detection device for protein in urine of the present invention.

With reference to FIG. 6, in another embodiment, after the sample urine 12 is dripped through of the needle 20, the sample urine 12 first forms the drop of urine 100 at the blunt end 22 of the needle 20, and then the drop of urine 100 drips down from the blunt end 22 of the needle 20. When the drop of urine 100 drips down from the blunt end 22, the detection beam passes through the drop of urine 100 and travels into the lens 41 of the camera unit 40 while the drop of urine 100 is falling in mid-air. As such, the image of the drop of urine 100 captured by the camera unit 40 resembles the drop of urine 100 free falling. The processor unit 60 receives the image from the camera unit 40, and proceeds to calculate the protein concentration of the sample urine 12 according to the image.

In the current embodiment, the processor unit 60 can predictively calculate the protein concentration of urine according to the image of the drop of urine 100 free falling. In the current embodiment, the processor unit 60 is an artificial intelligence (AI) model; in other words, the processor unit 60 is first trained according to big data, and then used to predict the protein concentration of the drop of urine 100 according to the shape of the drop of urine 100. The big data used to train the processor unit 60 includes the shapes of multiple drops of urine inputted into the AI model and multiple answers of protein concentration of urine outputted from the AI model. After training, and after analyzing the shape of the drop of urine 100 from the image, the processor unit 60 is able to reasonably predict the protein concentration expected of the drop of urine 100 according to the AI model stored and the shape of the drop of urine 100 inputted.

What is claimed is:

1. A detection device for protein in urine, comprising:
a urine container, including a urine containing area to contain a sample urine;
a needle, mounted at a bottom of the urine container, connecting the urine containing area, and having a first side and a second side; wherein the first side and the second side oppose each other; and wherein the first side is connected to the urine containing area, while the second side has a blunt end;
a base;
a holder, mounted on the base; wherein the urine container is detachably mounted on the holder, and the blunt end of the needle is mounted in suspension;
a camera unit, mounted on the base, and including a lens; wherein the lens of the camera unit is aimed at the blunt end;
a light source, mounted on the base, and emitting a detection beam; wherein the detection beam passes the blunt end and travels into the lens of the camera unit; and
a processor unit, electrically connecting the camera unit;
wherein, when the urine container contains the sample urine, the sample urine drips through the needle and forms a drop of urine;
wherein, after forming the drop of urine, the detection beam passes through the drop of urine and travels into the lens of the camera unit;
wherein, the processor unit receives an image of the drop of urine captured by the camera unit, and the processor unit calculates a protein concentration of the drop of urine according to the image;
wherein, when the sample urine drips through the needle, the sample urine forms the drop of urine at the blunt end of the needle;
wherein, when the processor unit calculates the protein concentration of the sample urine according to the image, the processor unit first calculates an averaged surface tension of the drop of urine according to the image, then the processor unit further calculates the protein concentration of the sample urine according to the averaged surface tension;
wherein, when the processor unit receives the image of the drop of urine through the camera unit, the processor unit further calculates a first drop diameter, a second drop diameter, and a correction coefficient from the image;
wherein, the first drop diameter is the widest diameter of the drop of urine in the image along a horizontal direction;
wherein, the second drop diameter is a diameter of a horizontal cross-section of the drop of urine in the image; wherein the horizontal cross-section is located vertically at the first drop diameter length away from a bottommost point of the drop of urine in the image; and wherein, the processor unit further uses a pendant drop method to calculate the averaged surface tension of the drop of urine according to the first drop diameter and the second drop diameter.

2. The detection device for protein in urine as claimed in claim 1, wherein, when the sample urine drips through the needle, the sample urine forms the drop of urine at the blunt end of the needle, and then the drop of urine drips down from the blunt end of the needle;

wherein, when the drop of urine drips down from the blunt end, the detection beam passes through the drop of urine and travels into the lens of the camera unit while the drop of urine is falling in mid-air;

wherein, the image captured by the camera unit resembles the drop of urine free falling.

3. The detection device for protein in urine as claimed in claim 2, wherein, the processor unit is an artificial intelligence (AI) model; wherein the processor unit is first trained according to big data, and then used to predict the protein concentration of the drop of urine according to a shape of the drop of urine;

wherein, the big data used to train the processor unit comprises shapes of multiple drops of urine inputted into the AI model and multiple answers of protein concentration of urine outputted from the AI model.

4. The detection device for protein in urine as claimed in claim 3, further comprising:

a diffuser, mounted between the light source and the blunt end of the needle;

wherein, when the detection light passes through the drop of urine and travels into the lens of the camera unit, the detection light first passes through the diffuser, and then further passes through the drop of urine and travels into the lens of the camera unit.

5. The detection device for protein in urine as claimed in claim 2, further comprising:

a diffuser, mounted between the light source and the blunt end of the needle;

wherein, when the detection light passes through the drop of urine and travels into the lens of the camera unit, the detection light first passes through the diffuser, and then further passes through the drop of urine and travels into the lens of the camera unit.

6. The detection device for protein in urine as claimed in claim 2, further comprising:

an input unit, electrically connected to the processor unit;

wherein when the input unit starts, the input unit sends a starting signal to the processor unit;

wherein when the processor unit receives the starting signal, the processor unit starts controlling the camera unit to capture the image of the drop of urine, and the processor unit receives the image.

7. The detection device for protein in urine as claimed in claim 6, further comprising:

a pressing unit, mounted on a side of the urine container, and electrically connected to the processor unit;

wherein after the processor unit receives the starting signal, the processor unit further starts the pressing unit, allowing the pressing unit to compress the side of the urine container, deforming a first deformation on the urine container, and allowing the sample urine to exit from the blunt end of the needle as the drop of urine with a first volume.

8. The detection device for protein in urine as claimed in claim 6, further comprising:

a pump unit, connected to a top side of the urine container, and electrically connected to the processor unit; wherein the pump unit produces a first outputting speed;

wherein after the processor unit receives the starting signal, the processor unit further starts the pump unit, allowing the pump unit to work for a first working time before stopping, and allowing the pump unit to output the drop of urine of the sample urine with the first volume from the urine container to the blunt end of the needle with the first outputting speed.

9. The detection device for protein in urine as claimed in claim 1, wherein, the processor unit stores a conversion table of the averaged surface tension to urine protein concentration;

wherein, when the processor unit calculates the protein concentration of the drop of urine according to the averaged surface tension, the processor unit uses the conversion table in order to correlate the protein concentration of the drop of urine.

10. The detection device for protein in urine as claimed in claim 1, further comprising:

a diffuser, mounted between the light source and the blunt end of the needle;

wherein, when the detection light passes through the drop of urine and travels into the lens of the camera unit, the detection light first passes through the diffuser, and then further passes through the drop of urine and travels into the lens of the camera unit.

11. The detection device for protein in urine as claimed in claim 1, further comprising:

an input unit, electrically connected to the processor unit;

wherein when the input unit starts, the input unit sends a starting signal to the processor unit;

wherein when the processor unit receives the starting signal, the processor unit starts controlling the camera unit to capture the image of the drop of urine, and the processor unit receives the image.

12. The detection device for protein in urine as claimed in claim 11, further comprising:

a pressing unit, mounted on a side of the urine container, and electrically connected to the processor unit;

wherein after the processor unit receives the starting signal, the processor unit further starts the pressing unit, allowing the pressing unit to compress the side of the urine container, deforming a first deformation on the urine container, and allowing the sample urine to exit from the blunt end of the needle as the drop of urine with a first volume.

13. The detection device for protein in urine as claimed in claim 11, further comprising:

a pump unit, connected to a top side of the urine container, and electrically connected to the processor unit; wherein the pump unit produces a first outputting speed;

wherein after the processor unit receives the starting signal, the processor unit further starts the pump unit, allowing the pump unit to work for a first working time before stopping, and allowing the pump unit to output the drop of urine of the sample urine with the first volume from the urine container to the blunt end of the needle with the first outputting speed.

* * * * *